(12) United States Patent
Rival et al.

(10) Patent No.: US 8,460,721 B2
(45) Date of Patent: Jun. 11, 2013

(54) ACTIVE INGREDIENT THAT STIMULATES THE PROLIFERATION AND/OR ACTIVITY OF FIBROBLASTS

(75) Inventors: Delphine Rival, Ternay (FR); Valérie Andre, Ampuis (FR); Louis Lamy, Orlienas (FR)

(73) Assignee: BASF Beauty Care Solutions France S.A.S., Lyons (FR)

( * ) Notice: Subject to any disclaimer, the term of this patent is extended or adjusted under 35 U.S.C. 154(b) by 0 days.

(21) Appl. No.: 12/935,965

(22) PCT Filed: Jun. 12, 2008

(86) PCT No.: PCT/EP2008/057372
§ 371 (c)(1),
(2), (4) Date: Nov. 16, 2010

(87) PCT Pub. No.: WO2009/121422
PCT Pub. Date: Oct. 8, 2009

(65) Prior Publication Data
US 2011/0052739 A1    Mar. 3, 2011

(30) Foreign Application Priority Data
Apr. 2, 2008 (FR) .................................. 08 52191

(51) Int. Cl.
*A61K 36/00* (2006.01)
*A61K 36/48* (2006.01)
(52) U.S. Cl.
USPC .............................. 424/757; 424/725; 424/776

(58) Field of Classification Search
None
See application file for complete search history.

(56) References Cited

U.S. PATENT DOCUMENTS

| 6,379,719 | B1 | 4/2002 | Gilles | |
|---|---|---|---|---|
| 2004/0091493 | A1 | 5/2004 | Perrier et al. | |
| 2004/0234560 | A1* | 11/2004 | Kimura et al. | 424/401 |
| 2005/0089499 | A1* | 4/2005 | Moussou et al. | 424/74 |

FOREIGN PATENT DOCUMENTS

| DE | 102005063062 A1 | | 7/2007 |
|---|---|---|---|
| JP | 10-029922 A | | 2/1998 |
| JP | 10029922 | * | 2/1998 |
| JP | 10029922 A | * | 2/1998 |

OTHER PUBLICATIONS

Tabor et al. The Revival Slim and Beautiful Diet. Thomas Nelson Inc. Apr. 3, 2007. p. 95.*

* cited by examiner

*Primary Examiner* — Qiuwen Mi
(74) *Attorney, Agent, or Firm* — Novak Druce Connolly Bove + Quigg LLP

(57) ABSTRACT

The invention relates to a novel active ingredient that stimulates the proliferation and/or the activity of fibroblasts and also to its applications in the cosmetic or pharmaceutical, in particular dermatological, field. In particular, the active ingredient according to the invention comprises a combination of at least one *Hibiscus Abelmoschus* extract and a soy extract containing at least peptides.

20 Claims, 1 Drawing Sheet

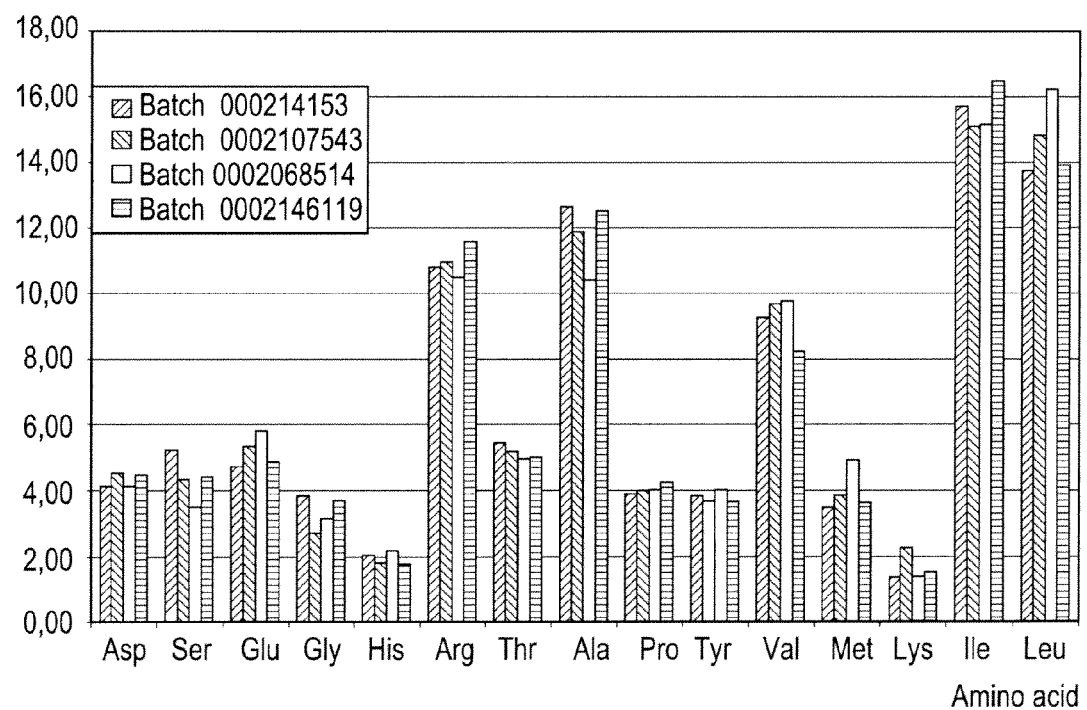

ACTIVE INGREDIENT THAT STIMULATES THE PROLIFERATION AND/OR ACTIVITY OF FIBROBLASTS

RELATED APPLICATIONS

This application is a national stage application (under 35 U.S.C. §371) of PCT/EP2008/057372, filed Jun. 12, 2008, which claims benefit of French application 0852191, filed Apr. 2, 2008.

The present invention relates to a novel active ingredient that stimulates the proliferation and/or the activity of fibroblasts and also to its applications in the cosmetic or pharmaceutical, in particular dermatological, field.

PRIOR ART

Fibroblasts are cells which enable the synthesis of macromolecules of the dermal extracellular matrix (ECM) such as collagen, elastin and glycosaminoglycans (GAGs). These macromolecules are essential to the integrity of the skin. With age and/or under the effect of various factors such as climatic and environmental factors, especially the wind, pollution, UV rays, cigarette smoke, and/or physiological factors, the dermal matrix has a tendency to atrophy, which is characteristic of skin ageing.

This atrophy is due to a decrease in the number of fibroblasts, to a reduction in their size and also to a reduction in the overall metabolism of the matrix and in particular a reduction of the syntheses of collagen, elastin and GAGs. It may result in a disruption of the ECM and be responsible for:
- a loss of the mechanical properties of the skin and/or of the mucous membranes, in particular the elasticity and firmness; and
- a loss of dermal reconstruction and/or regeneration capacity following an impairment of the dermal integrity of the skin and/or mucous membranes.

Skin ageing has, in particular, esthetic and/or uncomfortable consequences such as slackness of the tissues, loss of firmness, appearance of wrinkles, fine lines, grooves and/or stretch marks, and/or scars that are visible, uncomfortable and/or unaesthetic.

From a medical viewpoint, especially in dermatology, the skin and/or mucous membranes may be impaired, especially following inflammations, injuries, burns or surgical operations. Stimulating the proliferation and/or the activity of fibroblasts contributes to the resorption of scars so that they do not become pathological, and/or may contribute to preventing the appearance of inflammations such as gingivitis. This stimulation has an advantage for any type of damaged skin and/or mucous membranes and in particular for skin and/or mucous membranes that exhibit skin ageing.

The search for compounds and/or compositions capable of stimulating the proliferation of fibroblasts and/or their activity is therefore of great interest both in cosmetic fields for the cosmetic treatment and/or prevention of unaesthetic and/or uncomfortable manifestations due to skin ageing, and in pharmaceutical fields and in particular dermatological fields for preventing and/or treating the pathologies associated with ageing and/or impairments of the ECM.

The Applicant has already marketed a fermented soy extract containing peptides, known under the name of Phytokine™ and well known for its ability to stimulate the proliferation of fibroblasts. This soy peptide is also already known for its activity stimulating the synthesis of collagen, elastin and GAGs, and is used in cosmetics for its action on the firmness, especially in anti-ageing or slimming care products, and for its matrix-protecting action and its action on intensifying hydration. This Phytokine™ product has also been described in Patent Application EP 1 119 344 B1 (Laboratories Expanscience) for its action in preventing and/or treating stretch marks.

The Applicant has now just discovered that, very unexpectedly and surprisingly, this ability to stimulate the proliferation and/or the activity of fibroblasts may be further increased synergistically by the addition of a *Hibiscus Abelmoschus* extract. Tests carried out on fibroblasts as a monolayer in particular demonstrate this synergy (see example 2 below).

The Hibiscus extracts have already been described very generally in the prior art, especially for their cosmetic uses. Thus, an extract of *Abelmoschus moschatus* has been described for its ability to increase the hyaluronic acid content of the skin (JP 10-029922, Shiseido).

An aqueous extract of *Hibiscus Abelmoschus* obtained from the whole plant has also been described for its slimming properties in cosmetics, more particularly for combating cellulite (U.S. Pat. No. 5,705,170). Moreover, the Applicant has already described, in the French Patent Application filed under the number FR 0654316, the *Hibiscus Abelmoschus* extract according to the present invention for its ability to protect the fibroblast growth factor or FGF2 of the extracellular matrix against its degradation and/or its denaturation with the aim of restructuring the extracellular matrix. Nevertheless, by itself, said extract alone does not have the ability to stimulate the proliferation and/or the activity of fibroblasts (see example 2 below).

OBJECTIVE OF THE INVENTION

The objective of the invention is to provide novel active ingredients and compositions that stimulate the proliferation and/or the activity of fibroblasts and also its applications in the cosmetics or pharmaceutical, in particular dermatological, field.

In particular, the objective of the invention is to improve the properties of a soy extract that stimulate the proliferation and/or the activity of fibroblasts.

The invention also relates to novel applications of a hibiscus extract.

DESCRIPTION OF THE FIGURES

FIG. 1 represents the distribution of amino acids for several batches of *Hibiscus Abelmoschus* extract obtained according to Example 1.2)a).

DESCRIPTION OF THE INVENTION

One subject of the present invention is a novel active ingredient, especially a cosmetic, pharmaceutical, in particular dermatological or nutraceutical, ingredient comprising at least one extract of *Hibiscus Abelmoschus* and a soy extract containing at least peptides.

Another subject of the present invention are cosmetic, pharmaceutical, in particular dermatological or nutraceutical, compositions comprising said active ingredient.

Another subject of the present invention is the use of said active ingredient to stimulate the proliferation and/or the activity of fibroblasts in cosmetic or pharmaceutical and especially dermatological or nutraceutical applications.

A final subject of the present invention is the use of a *Hibiscus Abelmoschus* extract for increasing the proliferative activity of fibroblasts obtained with a soy extract containing at least peptides.

According to the present invention, the soy extract is an extract containing peptides, preferably obtained by hydrolysis of soy proteins. Advantageously, the soy extract is extracted from the soy seed, and contains at least peptides and has preferably been fermented by microorganisms, optionally in a medium enriched with fermentation sugars. Advantageously, the soy extract is a soy peptone. Preferably, the fermentation is carried out by lactic bacteria especially *Lactobacillus plantarum* or *Lactobacillus paracasei*, and/or by yeasts, in particular the genus *Saccharomyces*, preferably *Saccharomyces cerevisiae*.

Preferably, the microorganisms are then removed from the extract according to conventional techniques, especially by microcentrifugation or by filtration. Advantageously, the fermented extract is thus filtered over a membrane having a cut-off threshold of 0.45 µm in order to remove the microorganisms, and/or is filtered over a membrane having a cut-off threshold of 0.22 µm, in order to carry out a sterilizing filtration.

Such a soy extract has especially been marketed under the name Phytokine™ by the Applicant, and is especially described in Patent EP 1 119 344 B1 (Laboratoires Expanscience).

Particularly advantageously, the soy extract containing peptides, preferably obtained by fermentation, contains 6 main amino acids which are aspartic acid (Asp), glutamic acid (Glu), proline (Pro), glycine (Gly), alanine (Ala) and leucine (Leu), which are each preferably present in an amount of 5%, preferably 6% or more relative to the total amino acids of the extract.

Generally, the soy peptides in the composition used according to the present invention may be any peptide obtained by hydrolysis of proteins extracted from soy, according to operating conditions known to a person skilled in the art, in other words any soy protein hydrolysate. Preferably, these soy peptides are peptides that have additionally undergone a fermentation by a microorganism strain. Generally, a fermented soy peptide is obtained by placing a soy peptide in a fermenter in the presence of glucose, mineral salts and a given microorganism strain, under controlled temperature, pH, oxygenation and time conditions. After the fermentation, the fermented soy peptide is obtained by conventional separation and filtration operations.

Various fermented vegetable protein hydrolysates are thus marketed by the Applicant. Preferably, the fermented or unfermented soy peptides in the composition used according to the present invention have a molecular weight between around 200 and around 20 000 Da, as measured, for example, by electrophoresis. One soy extract containing such peptides that is particularly preferred according to the invention is the fermented soy extract known as "Phytokine™".

Preferably, the soy extract according to the invention, in particular the Phytokine™ product is used in an amount between 0.1% and 5% by weight of the final composition. A use between 1.25% and 3% by weight of the final composition makes it possible to obtain very good results.

The soy extract containing at least peptides, which is preferably fermented, may be in a dry form, especially a freeze-dried form or as a suspension in an aqueous solution or in a hydroalcoholic solution.

The *Hibiscus Abelmoschus* plant belongs to Malvaceae family, genus Hibiscus and is also known under the common name Ambrette.

The solvent for extraction and/or putting back into suspension may be any polar solvent as long as it makes it possible to obtain essentially all the active compounds in an aqueous extract in order to provide the properties desired within the context of the present invention. According to the tests carried out, the *Hibiscus Abelmoschus* extract is an aqueous extract, preferably obtained by extraction at ambient temperature (around 20° C. to around 30° C.) or at a temperature between 35 and 80° C. or is a hydroalcoholic, preferably hydroglycolic, extract of *Hibiscus Abelmoschus*. Among the hydroglycolic extracts, an extraction solvent of the water/glycol type is preferred. A water/butylene glycol mixture is particularly preferred. Among the non-hydroglycolic hydroalcoholic extracts, a water/methanol or water/ethanol solvent is particularly preferred.

The proportions of the water/alcohol mixture, preferably water/glycol mixture may vary as a person skilled in the art knows. The water/alcohol proportions are preferably between 10/90 and 90/10, and for example between 50/50 and 80/15.

Preferably, the extract is obtained from the *Hibiscus Abelmoschus* leaf or seed, preferably from the seed.

Said Hibiscus extract is obtained from 1 to 10% of the plant or part of the plant in the dry state relative to the weight of the total solution. The *Hibiscus Abelmoschus* extract may be used in an amount between 0.1% and 5% by weight of the final composition. Very good results are obtained with amounts between 1 and 3%, and preferably 2.25%, by weight of the final composition.

Such a product is also described in the Patent Application filed under the number FR 0654316.

The *Hibiscus Abelmoschus* extract may be in a dry form, especially a freeze-dried form, or in suspension in an aqueous solution or in the hydroalcoholic solution described previously.

Particularly advantageously, the *Hibiscus Abelmoschus* extract contains 5 main amino acids which are arginine, alanine, valine, leucine and isoleucine, which each represent at least 5%, preferably 6% or more than 6% of the total amino acids of the extract.

According to one advantageous embodiment, the active ingredient comprises at least one *Hibiscus Abelmoschus* extract and a preferably fermented soy extract, which is preferably fermented, containing at least peptides in a *Hibiscus Abelmoschus* extract/soy extract ratio between 1/1 and 1/5, preferably around 1/2.

The active ingredient may be obtained by simple mixing of the *Hibiscus Abelmoschus* extract and the fermented soy extract containing at least peptides.

The active ingredient according to the invention may be in any form suitable for its application to the skin and/or the mucous membranes. Preferably, it is in the form of an aqueous solution or in the hydroalcoholic solution described previously.

In one advantageous embodiment, the active ingredient is in liquid form and is incorporated into a patch, especially a liquid patch. A liquid patch that is particularly suitable for this purpose is especially made of an aqueous gel obtained by the combination of high molecular weight macromolecules which are polymers capable of forming a film-forming mesh at the surface of the skin. The polymers used for producing the patch may then be chosen from polysaccharides, proteins that have a film-forming effect and mixtures thereof. Among the polysaccharides, use will especially be made of gums, preferably gum acacia, and alginates, especially in the form of sodium, potassium, calcium or magnesium salts of alginic acid and preferably in the form of sodium alginates. Among the collagens, use will preferably be made of marine collagen, preferably those described in Patents FR 2678624 and FR 2801314 filed under the name of the Applicant (formerly Coletica). According to one particularly advantageous embodiment, the polymers used for producing the patch are sodium alginates and gum acacia and/or marine collagen. Such a patch is, in particular, known under the name Micropatch™, described in Patents FR 2678624 and FR 2801314 and marketed by the Applicant. The production of such a patch is especially described in example 7. The active ingredient according to the invention, alone or in combination with other active agents, especially serine, is then preferably added to the patch at a concentration between 10 and 90%, preferably between 1 and 50%. Said patch is then preferably used in an amount of 1 to 5% by weight in the final composition.

According to another particularly advantageous embodiment, the active ingredient according to the invention is encapsulated in a cosmetic and/or dermatological carrier suitable for topical application. This may include of nanoencapsulation, preferably liposomes, preferably cationic liposomes, and more preferably ones that open up under UV rays. Preferably, they are carriers described in Patents FR 8901221, FR 9202912, FR 934332, FR 2808691, FR 0216637, FR 2870741 filed in the name of the Applicant (formerly Coletica), especially those resulting from the combination of collagen and marine GAGS, the combination of propylene glycol alginates and acacia polysaccharides, the combination of lipophilized β-cyclodextrin and lauric acid, the combination of polymers of carob, wheat and acacia, the combination of soy lecithin and quaternized soy proteins. The production of such a liposome is especially described in example 3.

Another subject of the present invention is the use of the active ingredient for producing a cosmetic composition in combination with a cosmetic carrier suitable for topical application.

The cosmetic compositions according to the invention advantageously comprise an amount of soy extract containing peptides, preferably fermented, between 0.1% and 5%, preferably 1.25%, in combination with at least an amount of *Hibiscus Abelmoschus* extract between 0.1% and 5%, preferably 2.25%.

Advantageously, they contain other active agents of cosmetic interest especially the conventional agents for anti-ageing compositions especially those chosen from hyaluronic acid, ascorbic acid, retinol, alpha-hydroxy acids (AHAs) and/ or ursolic acid.

According to one advantageous embodiment, they contain at least one of the following agents:
  an agent that stimulates the fibronectin synthesis, in particular a maize extract, such an extract being sold, in particular, by the Applicant under the name Deliner™;
  an agent that stimulates the laminin synthesis, in particular an extract of malt modified by biotechnology, such an extract being sold, in particular, by the Applicant under the name Basaline™;
  an agent that stimulates the expression and/or the activity of hyaluronan synthase 2 (HAS2) such as the plant extracts described in Patent Application FR 2 893 252 A1 and in particular an aqueous extract of Galanga (*Alpinia galanga*);
  an agent that stimulates the synthesis of lysyl oxidase-like (LOXL) such as those described in Patent Application FR 2 855 968, and in particular the dill extract;
  an agent that stimulates the synthesis of intracellular ATP, especially an extract of alga *Laminaria digitata;*
  an agent that protects the degradation of FGF2.

The invention covers the concomitant, or sequential, use of a *Hibiscus Abelmoschus* extract and a soy extract containing at least peptides, which is preferably fermented, as defined previously, especially for increasing the activity of stimulating the proliferation and/or the activity of the fibroblasts of the soy extract.

The expression "sequential use" is understood to mean the use of the *Hibiscus Abelmoschus* and soy extracts separated and staggered, optionally according to a precise sequence, such as an alternate sequence of the extracts, optionally with a sequence comprising the successive use of the same extract. A sequence is typically determined by a person skilled in the art.

The expression "concomitant use" is understood to mean the separate and simultaneous use of the *Hibiscus Abelmoschus* and soy extracts.

Thus, the invention covers a composition kit and use thereof, said kit comprising, on the one hand, a composition comprising a *Hibiscus Abelmoschus* extract and, on the other hand, a composition comprising a soy extract containing at least peptides, as defined previously. These compositions may be packaged in a single kit or separately, for example in an identical, complementary or independent manner. These compositions may be formulated identically or differently. According to one advantageous mode, the soy extract containing at least peptides may be formulated in a patch, preferably a liquid patch such as described previously. The present invention also relates to such compositions containing either the soy extract containing at least peptides or the *Hibiscus Abelmoschus* extract and considered to be independently patentable.

Another subject of the present invention is the use of the active ingredient to stimulate the proliferation and/or the activity of fibroblasts, especially normal human fibroblasts, and especially for stimulating the synthesis of the macromolecules of the dermal extracellular matrix, in particular elastin, collagen and GAGs. The active ingredient additionally makes it possible to stimulate the renewal of the extracellular matrix, and in particular the dermal matrix and to improve dermic density.

According to the invention, the active ingredient, optionally in the form of the cosmetic compositions described previously, is particularly useful for the cosmetic care and/or the cosmetic treatment of the effects of skin ageing, especially unaesthetic and/or uncomfortable manifestations of skin ageing, such as slackness of the tissues, loss of firmness, the appearance of wrinkles, fine lines, and grooves, and/or stretch marks, and/or scars that are visible, uncomfortable and/or unaesthetic.

The active ingredient in its cosmetic applications optionally in the form of cosmetic compositions is particularly suitable for protecting the skin against skin ageing that is natural and/or caused by climatic and environmental factors, especially the wind, pollution, UV rays, cigarette smoke and/ or physiological factors, especially stress.

The invention also relates to a cosmetic care or treatment method, for a subject having need thereof, said method comprising the topical application or the administration, preferably orally, of a cosmetic composition according to the present invention to this subject.

In particular, a cosmetic care method in which the active ingredient and/or the cosmetic composition according to the invention are used via topical application to stimulate the proliferation and/or the activity of fibroblasts, especially for the cosmetic care and/or the cosmetic treatment of effects linked to skin ageing, especially unesthetic and/or uncomfortable manifestations of skin ageing, such slackness tissues, loss of firmness of the tissues, the appearance of wrinkles, fine lines, and grooves, and/or for the cosmetic treatment and/or care of stretch marks and/or scars.

In particular, the treatment or care method is intended to protect the skin against the effects of skin ageing, and in particular the effects cited in the present invention.

According to one embodiment, the cosmetic care or treatment method comprises the concomitant or sequential use of the extracts of the invention, as defined previously.

Advantageously, the subject who has need thereof is a subject chosen from a population having an average age of more than 30 years old.

Another subject of the present invention is a pharmaceutical, and in particular dermatological, composition containing said active ingredient optionally in combination with a pharmaceutical, especially dermatological, carrier suitable for its administration route.

The pharmaceutical compositions according to the invention advantageously comprise an amount of soy extract containing at least some fermented peptides between 0.1% and 5%, preferably 1.25%, in combination with at least an amount of *Hibiscus Abelmoschus* extract between 0.1% and 5%, preferably 2.25%. Advantageously, they contain other active agents and/or excipients and/or additives of pharmaceutical, especially dermatological, interest such as agents with the following properties:

wound-healing properties: such as panthenol and derivatives thereof, for example ethyl panthenol, aloe vera, pantothenic acid and derivatives thereof, allantoin, bisabolol, and dipotassium glycyrrhizinate;

anti-inflammatory properties: such as steroidal and non-steroidal anti-inflammatories, in particular Inhibitors of the production of cytokines and chemokines, of cyclooxygenase, of nitric oxide (NO) and nitric oxide synthase (NOS). As an example of anti-inflammatory products, mention may be made of extracts of Ginkgo biloba, trilactone terpenes such as ginkgolides, especially ginkgolide B and bilobalide known for their platelet-activating factor (PAF) antagonist properties.

According to the invention, the active ingredient can be used for producing pharmaceutical compositions, especially dermatological compositions, preferably intended for preventing and/or treating scars and/or inflammations such as gingivitis.

The pharmaceutical, especially dermatological, compositions are preferably intended for treating skin in which the dermis is at least partially damaged, especially in subjects who have undergone a surgical operation, or who have been burned and/or injured. This treatment makes it possible to stimulate the proliferation and/or the activity of fibroblasts, in order to stimulate tissue repair and/or dermal reconstruction.

The invention also relates to a pharmaceutical, preferably dermopharmaceutical, care or treatment method for a subject having need thereof, said method comprising the topical application or administration, preferably orally, of a pharmaceutical, preferably dermo-pharmaceutical, composition according to the present invention.

In particular, the pharmaceutical, preferably dermopharmaceutical, care or treatment method is intended for the applications cited in the present invention.

According to one embodiment, the pharmaceutical, preferably dermopharmaceutical, care or treatment method comprises the concomitant, sequential use of the extracts of the invention as defined previously.

Advantageously, the subject who has need thereof is a subject chosen from a population having an average age of more than 30 years old or who has skin for which the dermis is at least partially damaged, especially as explained in detail above.

The composition may contain any suitable solvent and/or any suitable carrier and/or any suitable excipient, optionally in combination with other compounds of interest.

Therefore, for the compositions according to the invention, the excipient contains, for example, at least one compound chosen from the group consisting of preservatives, emollients, emulsifiers, surfactants, moisturizers, thickeners, conditioners, matifying agents, stabilizers, antioxidants, texturizing agents, brighteners, film-forming agents, solubilizers, pigments, dyes, fragrances and sunscreens. These excipients are preferably chosen from the group consisting of amino acids and derivatives thereof, polyglycerols, esters, polymers and derivatives of cellulose, lanolin derivatives, phospholipids, lactoferrins, lactoperoxidases, sucrose-based stabilizers, vitamin E and derivatives thereof, natural and synthetic waxes, plant oils, triglycerides, unsaponifiable matter, phytosterols, plant esters, silicones and derivatives thereof, protein hydrolysates, jojoba oil and derivatives thereof, fat-soluble/water-soluble esters, betaines, aminoxides, plant extracts, saccharose esters, titanium dioxides, glycines and parabens, and more preferably from the group consisting of butylene glycol, steareth-2, steareth-21, glycol-15 stearyl ether, cetearyl alcohol, phenoxyethanol, methylparaben, ethylparaben, propylparaben, butylparaben, butylene glycol, natural tocopherols, glycerin, dihydroxycetyl sodium phosphate, isopropyl hydroxycetyl ether, glycol stearate, triisononanoin, octyl cocoate, polyacrylamide, isoparaffin, laureth-7, a carbomer, propylene glycol, glycerol, bisabolol, dimethicone, sodium hydroxide, PEG-30 dipolyhydroxystearate, capric/caprylic triglycerides, cetearyl octanoate, dibutyl adipate, grapeseed oil, jojoba oil, magnesium sulfate, EDTA, a cyclomethicone, xanthan gum, citric acid, sodium lauryl sulfate, waxes and mineral oils, isostearyl isostearate, propylene glycol dipelargonate, propylene glycol isostearate, PEG-8, beeswax, glycerides of hydrogenated palm kernel oil, glycerides of hydrogenated palm oil, lanolin oil, sesame oil, cetyl lactate, lanolin alcohol, castor oil, titanium dioxide, lactose, saccharose, low-density polyethylene, and an isotonic saline solution.

Advantageously, the aforementioned compositions are formulated in a form chosen from the group consisting of an aqueous or oily solution, a cream or an aqueous gel or an oily gel, especially in a pot or in a tube, especially a shower gel, a shampoo; a milk; an emulsion, a microemulsion or a nanoemulsion, especially one that is oil-in-water or water-in-oil or multiple or silicone-based; a mask; a lotion, especially in a glass or plastic bottle or in a measuring bottle or in an aerosol; an ampoule; a liquid soap; a dermatological cleansing bar; an ointment; a foam; an anhydrous product, preferably liquid, pasty or solid, for example in stick form especially in the form of lipstick or tablets.

According to the present invention, the expression "topical application" is understood to mean the application of the composition to the surface of the skin and/or the mucous membranes, especially gingival mucous membranes, in particular by direct application or by spraying.

The terms "suitable cosmetic or dermatological carrier" used here, mean that the composition or the components of the latter are suitable for use in contact with human skin without undue toxicity, incompatibility, instability, allergic response or their equivalents.

Many cosmetically active ingredients are known by a person skilled in the art for improving the health and/or the physical appearance of the skin. A person skilled in the art knows how to formulate the cosmetic or dermatological compositions to obtain the best effects. On the other hand, the compounds described in the present invention may have a synergistic effect when they are combined one with another. These combinations are also covered by the present invention. The CTFA Cosmetic Ingredient Handbook, Second Edition (1992) describes various cosmetic and pharmaceutical ingredients commonly used in the cosmetic and pharmaceutical industry, which are in particular suitable for topical use. Examples of these classes of ingredients comprise, without being limited thereto, the following compounds: abrasives, absorbents, compounds having an esthetic purpose such as fragrances; pigments; dyes; essential oils; astringents such as clove oil, menthol, camphor, eucalyptus oil, eugenol, menthyl lactate, witch hazel distillate; anti-acne agents; anti-flocculating agents; antifoaming agents; antimicrobial agents such as iodopropyl butylcarbamate; antioxidants such as ascorbic acid; binders; biological additives; buffers; swelling agents; chelating agents; additives; biocides; denaturants; thickeners; and vitamins; film-forming materials; polymers; opacifiers; pH modifiers; reducing agents; conditioning agents such as humectants, and derivatives or equivalents of the latter.

FIG. 1 represents the distribution of amino acids for several batches of *Hibiscus Abelmoschus* extract obtained according to Example 1.2)a).

The examples below are an integral part of the present invention and serve to illustrate it without, however, constituting a limitation thereof. Any feature that appears novel with respect to any prior art based on the description taken in its entirety, including the examples, is an integral part of the invention functionally and generally.

EXAMPLES

Example 1

Production of the Active Ingredient According to the Invention 1.1) A 1st soy extract product was produced. A soy seed peptone was fermented by a *Lactobacillus* microorganism. Such a product is sold by the Applicant under the name Phytokine™, known and described in Patent EP 1 119 344 61 (Laboratoires Expanscience).

This product had an average molecular weight of around 800 Da and had the following aminogram:

TABLE 1

| Aminogram of the soy extract containing at least some fermented peptides: | |
|---|---|
| | Number of residues per 100 |
| Hyp | 0.00 |
| Asp | 12.13 |
| Thr | 3.04 |
| Ser | 3.62 |
| Glu | 18.15 |
| Pro | 6.78 |
| Gly | 8.84 |
| Ala | 9.97 |
| Cys | ND |
| Val | 5.37 |
| Met | 1.30 |
| Ile | 4.42 |
| Leu | 7.42 |
| Tyr | 2.10 |
| Phe | 3.60 |
| His | 1.81 |
| Lys | 5.71 |
| Trp | ND |
| Arg | 5.73 |
| β-Ala | ND |

ND = Not determined 1.2) Several examples for obtaining an extract of *Hibiscus Abelmoschus* (ambrette) are described below:

a) A *Hibiscus Abelmoschus* extract was obtained by extraction from the seed. This extract was produced from ground seeds at 5% (w/w) in ethanol under reflux or in a 75% water/25% mixture, preferably in water. The maceration was carried out for 1 night at 4° C. or ambient temperature or preferably for 2 hours at ambient temperature.

The solution was ultrafiltered over ceramic filters having various cut-off thresholds and especially at 0.45 µm.

The product obtained has a particularly characteristic distribution of free amino acids which is described in FIG. 1, and which represents the distribution of amino acids of several batches of *Hibiscus Abelmoschus* extract obtained according to 1.2)a) (distribution in wt % of amino acid relative to the total weight of the amino acids of the batch in question).

Several industrial batches of such a product were studied and 5 main amino acids were observed in a significant manner for each batch, namely arginine, alanine, valine, leucine and isoleucine.

b) A hydroalcoholic extract of *Hibiscus Abelmoschus* was produced from ground seeds at 5% (w/w) in ethanol under reflux. The extraction was carried out for 1 hour, then the solution was filtered, the ethanol removed, and the resulting product was dissolved at 5% (w/w) in a water/glycol (75/25) mixture then ultrafiltered over ceramic filters having various cut-off thresholds, and finally filtered at 0.45 µm.

c) A hydroglycolic extract of *Hibiscus Abelmoschus* was produced in a water (75%)/butylene glycol (25%) mixture, preferably from ground seeds at 5% (w/w). The maceration was carried out over 1 night at 4° C., then the solution was ultrafiltered over ceramic filters having various cut-off thresholds, and finally filtered at 0.45 µm.

d) An aqueous extract of *Hibiscus Abelmoschus* was produced in water, preferably from ground seeds at 5% (w/w). The maceration was carried out over 1 night at 4° C., then the solution was ultrafiltered over ceramic filters having various cut-off thresholds, and finally filtered at 0.45 µm.

1.3) The active ingredient was then obtained by pie mixing of the two soy and *Hibiscus Abelmoschus* extracts.

Example 2

Study of Cellular Proliferation on Normal Human Fibroblasts as a Monolayer

1) Material and Methods:

Normal human dermal fibroblasts obtained from an abdomen surgery of a 34-year-old donor, were seeded at a low density in 6-well culture plates. They were cultivated in the DMEM (Dubbelco Modified Eagle Medium) medium for 48 hours in the absence (untreated control) or in the presence of the products to be tested at various concentrations.

The products tested were the product Phytokine™ (according to Example 1.1), the *Hibiscus Abelmoschus* extract (hereinafter Hibiscus ext.) (according to Example 1.2 a), and the combination thereof.

At sub-confluence, the cells were treated according to the conditions below:
untreated (no product);
positive control (10% fetal veal serum);
1.25% Phytokine™;
0.125% or 0.25% Hibiscus ext.;
1.25% Phytokine™+0.125% Hibiscus ext.;
1.25% Phytokine™+0.25% Hibiscus ext.

After incubating for 48 hours at 37° C., the medium was removed then a p-nitrophenyl phosphate (pnpp) assay was carried out. This assay was based on the conversion of p-nitrophenyl phosphate (pnpp) to p-nitro-phenol by the intracellular acid phosphatases of the viable cells. The absorbance of p-nitrophenol at 405 nm is directly proportional to the number of viable cells contained in the culture wells and therefore consequently makes it possible to evaluate the cellular proliferation in comparison with the untreated wells.

For this purpose, after removing the medium, the cells were rinsed then brought into contact with a buffer containing 5 mM of p-nitrophenyl phosphate (Sigma, France), After incubating at 37° C. in an atmosphere containing 5% $CO_2$, the reaction was stopped by addition of 1N NaOH. The absorbance of the medium at 405 nm was then determined using a plate reader (Victor$^2$ V, Perkin Elmer, Finland).

The non-enzymatic hydrolysis of the p-nitrophenyl phosphate was determined during each experiment on the (blank) wells that did not contain cells.

2) Results:

For each product tested, the results were expressed as a percentage of cellular proliferation (hereinafter cell. prolif.) relative to the untreated control. All the measurements were carried out in sextuplate (n=6).

The results were expressed as the average+/−standard deviation (SD). The statistics between the groups were carried out by a one-way ANOVA test/Dunnett test (*: $p<0.05$, : $p<0.01$, *: $p<0.001$). The results obtained are described in the table below:

TABLE 2

Stimulation of cell proliferation of fibroblasts:

| Condition | Average | Standard deviation | Cell. prolif. (%) vs. control | Cell. prolif. (%) vs. Phytokine ™ |
|---|---|---|---|---|
| Untreated | 0.267 | 0.005 | 100 | — |
| Positive control | 0.441 | 0.019 | 165 $p < 0.001$ | — |
| 1.25% Phytokine ™ | 0.359 | 0.014 | 134 $p < 0.001$ | 100 |
| 0.125% *Hibiscus* ext. | 0.257 | 0.010 | 96 ns | — |
| 0.25% *Hibiscus* ext. | 0.281 | 0.008 | 105 $p < 0.01$ | — |
| Phytokine ™ + 0.125% *Hibiscus* ext. | 0.381 | 0.016 | 143 $p < 0.001$ | 106 $p < 0.05$ |
| Phytokine ™ + 0.25% *Hibiscus* ext. | 0.439 | 0.017 | 165 $p < 0.001$ | 122 $p < 0.001$ |

It has been observed that the positive experimental control composed of 10% of fetal veal serum stimulated the proliferation of fibroblasts by +165%. This is the expected result which validates this experiment.

The addition of 1.25% Phytokine™ alone stimulated the cellular proliferation by +134% ($p<0.001$) in a significant manner relative to the untreated control. This result was also expected since Phytokine™ is known for stimulating the proliferation of fibroblasts under these experimental conditions.

The addition of 0.125% *Hibiscus Abelmoschus* extract alone did not stimulate the proliferation of fibroblasts.

The addition of a larger amount of *Hibiscus Abelmoschus* extract (0.25%) weakly stimulated the proliferation of fibroblasts (+105%).

The combination according to the present invention of Phytokine™+0.125% *Hibiscus Abelmoschus* extract stimulated the proliferation significantly not only relative to the untreated control (+143%) but also relative to Phytokine™ used alone (+106% vs PHK).

The combination according to the present invention of Phytokine™+0.25% *Hibiscus Abelmoschus* extract very significantly stimulated the proliferation not only relative to the untreated control (+165%) but also relative to Phytokine™ used alone (+122%).

Thus, a real synergistic action is observed by the use of the combination according to the invention, in particular Phytokine™ and the *Hibiscus Abelmoschus* extract, on the proliferation of normal human fibroblasts.

Example 3

Compositions According to the Invention

The methods known to a person skilled in the art were followed for mixing together the various parts A, B, C, D, E, or F in order to prepare a composition according to the present invention.

The "products of the invention" represent the active ingredients mentioned in the present invention, especially the active ingredient obtained by mixing the product Phytokine™ prepared as indicated in Example 1.1) and the *Hibiscus Abelmoschus* extract prepared according to Example 1.2 a), b), c), or d), and preferably according to Example 1.2a).

The products of the invention may also be present in the form of liposomes containing 5% of soy lecithin and incorporating a quaternized soy solution (600 g at the end) obtained according to the following embodiment:

30 g of soy lecithin, 12 g of quaternized soy solution, 7.5 g of soy extract obtained according to Example 1.1) and 1.5 g of *Hibiscus Abelmoschus* extract prepared according to Example 1.2 a) were introduced into a pill-making machine and diluted in 447 g of pure laboratory water.

After stirring magnetically for 10 minutes at ambient temperature, the mixture was homogenized vigorously for 10 minutes, thus obtaining a liposomal solution in which the liposomes had an average size which could vary between 100 and 800 nanometers according to the exact homogenization conditions.

The suspension was then gently stirred for 1 hour. 90 g of butylene glycol, 6 g of phenoxyethanol and 6 g of hydroxyethyl cellulose (gelling agent) were then added.

| Formulation 3a: | | |
|---|---|---|
| A | Water | qs for 100 |
| | Butylene glycol | 2 |
| | Glycerin | 3 |
| | Sodium dihydroxycetyl phosphate, isopropyl hydroxycetyl ether | 2 |
| B | Glycol stearate SE | 14 |
| | Triisononaoin | 5 |
| | Octyl cocoate | 6 |
| C | Butylene glycol, methylparaben, ethylparaben, propylparaben, pH adjusted to 5.5 | 2 |
| D | Products of the invention | 0.01-10% |
| Formulation 3b: | | |
| A | Water | qs for 100 |
| | Butylene glycol | 2 |
| | Glycerin | 3 |
| | Polyacrylamide, isoparaffin, laureth-7 | 2.8 |
| B | Butylene glycol, methylparaben, ethylparaben, propylparaben; | 2 |

-continued

|   |                                                                                  |             |
|---|----------------------------------------------------------------------------------|-------------|
|   | Phenoxyethanol, methylparaben, propylparaben, butylparaben, ethylparaben         | 2           |
|   | Butylene glycol                                                                  | 0.5         |
| D | Products of the invention                                                        | 0.01-10%    |

Formulation 3c:

|   |                                                                        |             |
|---|------------------------------------------------------------------------|-------------|
| A | Carbomer                                                               | 0.50        |
|   | Propylene glycol                                                       | 3           |
|   | Glycerol                                                               | 5           |
|   | Water                                                                  | qs for 100  |
| B | Octyl cocoate                                                          | 5           |
|   | Bisabolol                                                              | 0.30        |
|   | Dimethicone                                                            | 0.30        |
| C | Sodium hydroxide                                                       | 1.60        |
| D | Phenoxyethanol, methylparaben, propylparaben, butylparaben, ethylparaben | 0.50      |
| E | Fragrance                                                              | 0.30        |
| F | Products of the invention                                              | 0.01-10%    |

Example 4 of the Invention

Use of the Products of the Invention in a Water-in-Oil Type Formulation

|   |                                                                                  |             |
|---|----------------------------------------------------------------------------------|-------------|
| A | PEG-30 dipolyhydroxystearate                                                     | 3           |
|   | Capric triglycerides                                                             | 3           |
|   | Cetearyl octanoate                                                               | 4           |
|   | Dibutyl adipate                                                                  | 3           |
|   | Grape seed oil                                                                   | 1.5         |
|   | Jojoba oil                                                                       | 1.5         |
|   | Phenoxyethanol, methylparaben, propylparaben, butylparaben, ethylparaben         | 0.5         |
| B | Glycerin                                                                         | 3           |
|   | Butylene glycol                                                                  | 3           |
|   | Magnesium sulfate                                                                | 0.5         |
|   | EDTA                                                                             | 0.05        |
|   | Water                                                                            | qs for 100  |
| C | Cyclomethicone                                                                   | 1           |
|   | Dimethicone                                                                      | 1           |
| D | Fragrance                                                                        | 0.3         |
| E | Products of the invention                                                        | 0.01-10%    |

Example 5 According to the Invention

Use of the Products of the Invention in a Shampoo or Shower Gel Type Formulation

|   |                                                                                  |             |
|---|----------------------------------------------------------------------------------|-------------|
| A | Xanthan gum                                                                      | 0.8         |
|   | Water                                                                            | qs for 100  |
| B | Butylene glycol, methylparaben, ethylparaben, propylparaben                      | 0.5         |
|   | Phenoxyethanol, methylparaben, propylparaben, butylparaben, ethylparaben         | 0.5         |
| C | Citric acid                                                                      | 0.8         |
| D | Sodium laureth sulfate                                                           | 40.0        |
| E | Product of the invention                                                         | 0.01-10%    |

Example 6 of the Invention

Use of the Products of the Invention in a Formulation of Aqueous (Eye Contour, Slimming, etc.) Gels

|   |                                                                                  |             |
|---|----------------------------------------------------------------------------------|-------------|
| A | Water                                                                            | qs for 100  |
|   | Carbomer                                                                         | 0.5         |
|   | Butylene glycol                                                                  | 15          |
|   | Phenoxyethanol, methylparaben, propylparaben, butylparaben, ethylparaben         | 0.5         |
| B | Products of the invention                                                        | 0.01-10%    |

Example 7 of the Invention

Use of the Products of the Invention in a Liquid Patch Formulation 20 g of soy extract obtained according to Example 1.1) and 20 g of *Hibiscus Abelmoschus* extract prepared according to Example 1.2 a) were mixed with 38 g of deionized water. Added to this mixture were 1% of sodium alginate and 1% of marine collagen. Finally, 20 g of butylene glycol containing preservatives were added.

This patch may be used alone or formulated in another conventional cosmetic composition.

Example 8 of the Invention

Preparation of Pharmaceutical Formulations Containing the Product of the Invention

|   | Formulation 8a: Preparation of tablets |                  |
|---|----------------------------------------|------------------|
| A | Excipients                             | in g per tablet  |
|   | Lactose                                | 0.359            |
|   | Sucrose                                | 0.240            |
| B | Products of the invention              | 0.001-0.1        |

|   | Formulation 8b: Preparation of an ointment |            |
|---|--------------------------------------------|------------|
| A | Excipients                                 |            |
|   | Low-density polyethylene                   | 5.5        |
|   | Liquid paraffin                            | qs for 100 |
| B | Products of the invention                  | 0.001-0.1  |

The invention claimed is:

1. An active ingredient comprising at least one extract of *Hibiscus Abelmoschus* and a soy extract containing at least peptides wherein the *Hibiscus abelmoschus* extract is used in an amount between 0.1% and 5% by weight of the final composition, and the soy extract is used in an amount between 0.1% and 5% by weight of the final composition.

2. The active ingredient as claimed in claim 1, in which the *Hibiscus Abelmoschus* extract is obtained from seeds.

3. The active ingredient as claimed in claim 1, in which the *Hibiscus Abelmoschus* extract is an aqueous extract, a hydroalcoholic extract, or a hydroglycolic extract.

4. The active ingredient as claimed in claim 1, in which the soy extract containing at least peptides is obtained by fermentation.

5. The active ingredient as claimed in claim 4, wherein the fermentation is carried out by bacteria and/or by yeast.

6. The active ingredient as claimed in claim 5, wherein the bacteria is *Lactobacillus plantarum* or *Lactobacillus paracasei*.

7. The active ingredient as claimed in claim 5, wherein the yeast is *Saccharomyces cerevisiae*.

8. The active ingredient as claimed in claim 1, in which the soy extract is filtered through a membrane having a cut-off threshold of 0.45 μm and/or 0.22 μm.

9. The active ingredient as claimed in claim 1, in which the soy extract is a fermented soy extract in a *Hibiscus Abelmoschus* extract/soy extract ratio between 1/1 and 1/5.

10. A cosmetic composition containing the active ingredient as claimed in claim 1, in combination with a cosmetic carrier suitable for topical application.

11. A cosmetic care method comprising topically applying:
  a) an active ingredient comprising at least one extract of *Hibiscus Abelmoschus* and a soy extract containing at least peptides wherein the *Hibiscus abelmoschus* extract is used in an amount between 0.1% and 5% by weight of the final composition, and the soy extract is used in an amount between 0.1% and 5% by weight of the final composition; and/or
  b) the cosmetic composition as claimed in claim 10, wherein said active ingredient and/or said cosmetic composition stimulates the proliferation and/or activity of fibroblasts.

12. A method for the cosmetic care and/or the cosmetic treatment of effects linked to skin ageing and/or for the cosmetic treatment and/or care of stretch marks and/or scars, comprising topically applying
  a) an active ingredient comprising at least one extract of *Hibiscus Abelmoschus* and a soy extract containing at least peptides wherein the *Hibiscus abelmoschus* extract is used in an amount between 0.1% and 5% by weight of the final composition, and the soy extract is used in an amount between 0.1% and 5% by weight of the final composition; and/or
  b) the cosmetic composition as claimed in claim 10.

13. A method for protecting the skin against skin ageing, comprising administering the active ingredient as claimed in claim 1.

14. A pharmaceutical composition containing the active ingredient as claimed in claim 1.

15. A method for treating scars and/or inflammation comprising topically applying the pharmaceutical composition as claimed in claim 14.

16. The method as claimed in claim 11, in which the at least one extract of *Hibiscus Abelmoschus* and the soy extract containing at least peptides are used concomitantly.

17. The active ingredient as claimed in claim 9, in which the *Hibiscus Abelmoschus* extract/soy extract ratio is around 1/2.

18. The method as claimed in claim 9, wherein the at least one extract of *Hibiscus Abelmoschus* extract and the soy extract containing at least peptides are used sequentially.

19. The method as claimed in claim 12, wherein the effects linked to skin ageing are unaesthetic and/or uncomfortable manifestations of skin ageing selected from the group consisting of:
  a) slackness of the tissues;
  b) loss of firmness of the tissues; and
  c) the appearance of wrinkles, fine lines, and grooves.

20. The method as claimed in claim 15, wherein the inflammation is gingivitis.

* * * * *

UNITED STATES PATENT AND TRADEMARK OFFICE
CERTIFICATE OF CORRECTION

PATENT NO.       : 8,460,721 B2
APPLICATION NO.  : 12/935965
DATED            : June 11, 2013
INVENTOR(S)      : Rival et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 17 days.

Signed and Sealed this
Eighth Day of September, 2015

Michelle K. Lee
*Director of the United States Patent and Trademark Office*